United States Patent
Hock et al.

(10) Patent No.: US 8,501,082 B2
(45) Date of Patent: Aug. 6, 2013

(54) METHOD FOR PRODUCING A MULTIPART CONSTRUCTION AND SUCH A CONSTRUCTION

(75) Inventors: Elmar Hock, Mombris-Konigshofen (DE); Stefan Fecher, Johannesberg (DE); Lothar Volkl, Goldbach (DE)

(73) Assignee: Degudent GmbH, Hanau (DE)

( * ) Notice: Subject to any disclaimer, the term of this patent is extended or adjusted under 35 U.S.C. 154(b) by 425 days.

(21) Appl. No.: 12/516,272

(22) PCT Filed: Dec. 21, 2007

(86) PCT No.: PCT/EP2007/064477
§ 371 (c)(1),
(2), (4) Date: May 26, 2009

(87) PCT Pub. No.: WO2008/080902
PCT Pub. Date: Jul. 10, 2008

(65) Prior Publication Data
US 2010/0062396 A1 Mar. 11, 2010

(30) Foreign Application Priority Data

Dec. 27, 2006 (DE) .......................... 10 2006 062 305
Feb. 7, 2007 (EP) ..................................... 07002574

(51) Int. Cl.
*B28B 3/00* (2006.01)
(52) U.S. Cl.
USPC ....................................................... 264/667
(58) Field of Classification Search
USPC .............................................. 264/605, 667
See application file for complete search history.

(56) References Cited

U.S. PATENT DOCUMENTS

| | | | |
|---|---|---|---|
| 4,969,913 A | 11/1990 | Ojima | |
| 5,290,332 A * | 3/1994 | Chatterjee et al. | 65/17.3 |
| 6,106,747 A | 8/2000 | Wohlwend | |
| 2008/0241551 A1* | 10/2008 | Zhang et al. | 428/428 |

FOREIGN PATENT DOCUMENTS

| | | |
|---|---|---|
| DE | 3122345 | 12/1982 |
| JP | 61040884 | 2/1986 |
| JP | 4-248013 | 9/1992 |

OTHER PUBLICATIONS

Machine translation of DE 3122345 specification.*

* cited by examiner

*Primary Examiner* — Joseph S Del Sole
*Assistant Examiner* — Russell Kemmerle, III
(74) *Attorney, Agent, or Firm* — Ladas & Parry, LLP

(57) ABSTRACT

A method for manufacturing a multipart assembly of sintered oxide ceramic material, including one first component which at least partially surrounds one second component in such a manner that detaching the first component from the second component is not possible without destroying the first and/or second component. The assembly is produced by producing a single-part first shaped part and a single-part second shaped part from an oxide ceramic blank, whereby the first shaped part and the second shaped part are enlarged to compensate for the shrinkage during sintering, and assembling the sintered shaped part as second component with the first shaped part and subsequently sintering them together. As the first shaped part is employed a shaped part with an opening whose effective cross section after sintering is either smaller than the effective cross section of the second shaped part after sintering in a region that extends within the first component, or is smaller that the effective cross section of the second component in front of and behind the opening.

32 Claims, 4 Drawing Sheets

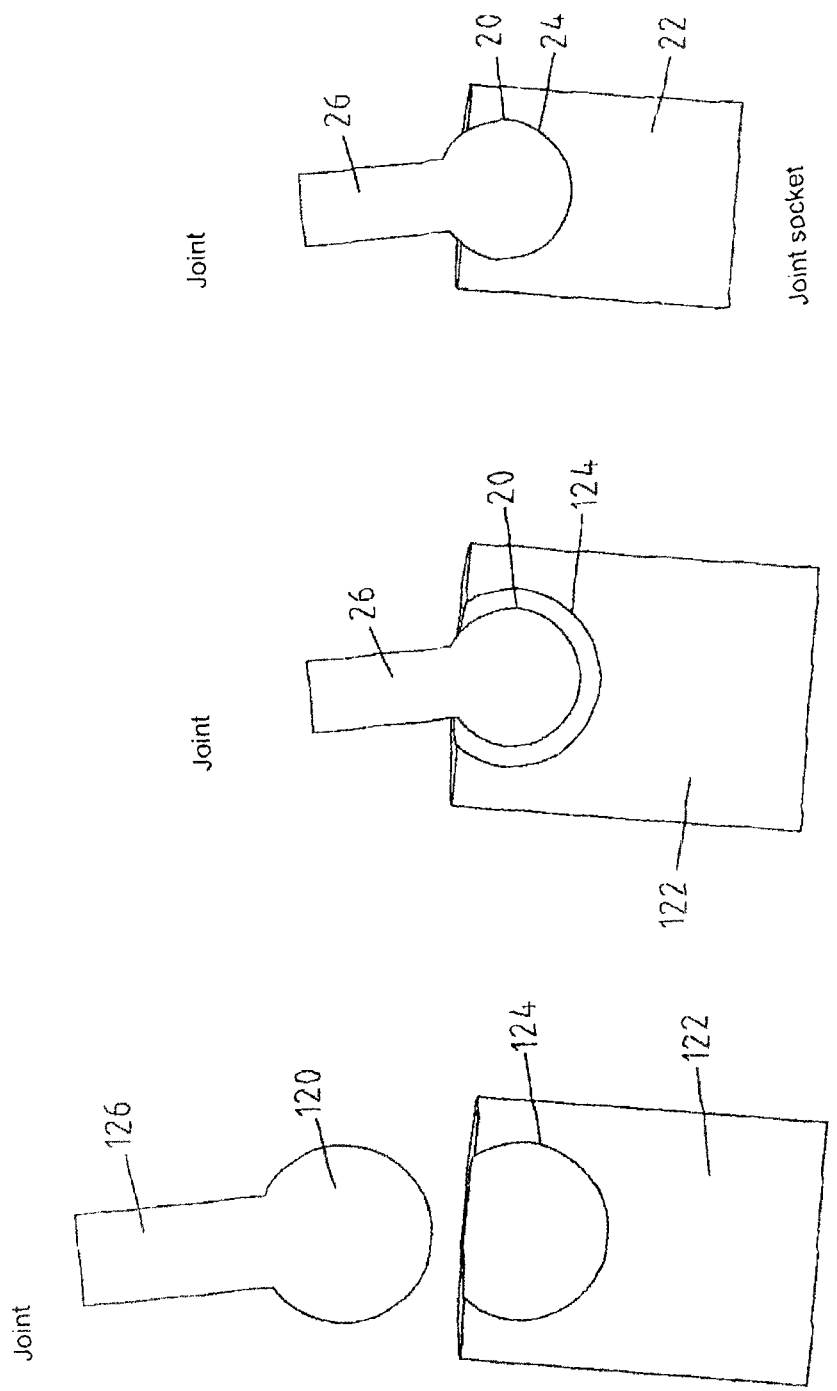

METHOD FOR PRODUCING A MULTIPART CONSTRUCTION AND SUCH A CONSTRUCTION

The invention relates to a method for manufacturing a multipart assembly from sintered oxide ceramic material, such as partially stabilized zirconia, comprising one first component that at least partially surrounds a second component, employing the process steps:
- producing one first shaped part and one second shaped part from an oxide ceramic blank, whereby the first shaped part and the second shaped part are enlarged—relative to the first and the second component—by a scaling factor that compensates for shrinkage during sintering,
- sintering of the shaped part that is at least partially surrounded by the other shaped part,
- assembling the sintered shaped part as the second component with the first shaped part and subsequently sintering them together.

Ceramic materials, in particular zirconium oxide, are widely employed as technical ceramics in mechanical engineering on account of their thermal stability, particularly because of their low wear characteristics. On account of their biological compatibility and chemical inertness, ceramic materials are also employed in dentistry in the manufacture of crown and bridge structures using CAD/CAM processes, dental root posts, and metal-free dental implants. The corresponding components generally are manufactured by at first producing a blank, which is then machined by for example milling, whereby one at first creates a larger shaped part that is enlarged relative to the final shaped part by a scaling factor that compensates for shrinkage during sintering. This results in easier machining, allowing the manufacture of high-precision small components.

Examples of application in dentistry can be found in WO-A-99/47065 or WO-A-96/29951.

Technical components that already are being manufactured using corresponding methods for example include nozzles, valves, pump components, thread guides, locating pins for welding, or screw threads.

In multipart assemblies, a component that is intended to accommodate another component must consist of several parts, since assembly is impossible otherwise.

A method of the above-mentioned type is described by DE-A-31 22 345. Here, the first part possesses a bore, into which the second part is centrically placed. Since the second part has been sintered already and the exterior part, i.e. first part, is subject to the complete shrinkage during the sintering process, the contacting surfaces of the parts are subjected to a press fit during the sintering process, which leads to a complete fusion of the contact surfaces. A relative movement is no longer possible.

In order to obtain an interference fit between two parts, GB-A-2 210 363 describes how into a bore of an outer porous body of ceramic is inserted a section of an inner, denser body of ceramic, whereupon the bodies are sintered together.

The present invention is based on the objective to make available a method of the above-mentioned type as well as a multipart assembly consisting of completely sintered oxide ceramic material, without the need for individual components to consist of multiple parts to facilitate assembly.

According to this invention's method, this objective is met by using one-piece shaped parts as each of the first shaped part and the second shaped part, by completely sintering the second shaped part to produce the second component, and by positioning the first shaped part in a region of the second component, where—after sintering the first shaped part and the second component together—the first component produced by complete sintering is surrounded by the second component in such a manner that detaching the first component from the second component becomes impossible without destroying the first and/or the second component.

In particular, it is intended to use as a first shaped part a shaped part with an opening, which possesses an effective cross-section after complete sintering that either is smaller than the effective cross-section of the second shaped part after complete sintering in a region that extends within the first component, or is smaller than the effective cross-section of the second component in front of and behind the opening.

The teaching of the invention creates the possibility of joining together constructional elements, which—owing to their final geometries—could otherwise not be assembled without splitting up one of the parts. An example of this is a plunger rod with a plunger passing through an opening in a casing, whereby the diameter of the plunger is greater than that of the opening. If the plunger is sintered first and if the casing is present in the form of a blank or presintered blank, the casing's opening will be significantly larger than in its final state, as a result of which the completely sintered plunger rod with plunger can pass through the opening. During a subsequent complete sintering, the casing shrinks to such a degree that the predetermined precise fit of the geometries of the casing and the plunger rod with plunger is achieved. During a repeated heat treatment, the shape of the piston will not change.

In accordance with the invention, it is possible to produce multipart assemblies, where the individual component parts must adhere to a precisely defined relative alignment and correspondence. Ceramic blanks are used to produce the single-part component parts in a size that is scaled up by the sinter-shrinkage factor in all directions, so that the shrinkage of sintering is subsequently compensated for. Subsequently, at least the shaped part that is to be surrounded by another component is completely sintered. After this, the completely sintered component is assembled together with the other component that has not yet been completely sintered and subsequently both components are completely sintered together. This yields an overall assembly with defined alignment and correspondence of the individual components, so components such as pivot bearings, thrust bearings, interference fits, or similar can be achieved to a desired extent, without the need to embody the individual parts as multipart components. Also achievable is a high accuracy of fit, with any amount of possibly desired clearances between the first and the second component in the completely sintered state, i.e. the final state.

Suitable for use as a blank are green blanks of pressed oxide ceramic powder or presintered blanks of pressed oxide ceramic powder. Both of these starting materials facilitate ease of operation, whereby the enlarged shape—relative to the final part—allows processing that yields a high-precision final geometry.

As oxide ceramic powder, at least one metal oxide powder out of the group $AL_2O_3$, $TiO_2$, $Y_2O_3$, $BaTiO_3$, zirconia, zirconia mixed crystal, should be used. In particular it is intended to employ a zirconia powder that is offered by TOSOH under the trade name 3Y-TZP.

In particular, one employs a zirconia powder with a composition of:

| | |
|---|---|
| 90-98% by weight | zirconia |
| 0-4% by weight | hafnium oxide |
| 1-7% by weight | yttrium oxide |
| 0-1% by weight | one of the oxides of the elements aluminium, gallium, germanium, indium, zinc, lead, the lanthanides |
| 0-2% by weight | oxidation-dyeing additives. |

Suitable oxidation-dye additives are $Er_2O_3$, $Pr_6O_{11}$, or $Fe_2O_3$.

The oxide ceramic powder itself is at first pressed, in particular using isostatic pressing at a pressure P with 150 MPa$\leq$P$\leq$350 MPa, with a preferred pressure of approximately 200 MPa, to subsequently be presintered—possibly after a heat pre-treatment. Preferred temperatures are in a range between 600° C. and 1200° C., whereby a duration between 0.5 hours and 6 hours should be chosen. Particularly good results are obtained when presintering for 2 hours at approximately 850° C.

Naturally, axial pressing is also possible.

The complete sintering itself should be carried out in the temperature region between 1300° C. and 1650° C. for a duration between 1 h to 3 h, whereby preferred values are 1500° C. and 2 h.

Independent hereof, the complete sintering should be performed to such a degree that the blank is dense-sintered to between 90% and 100%, preferably between 96% and 100%, of the theoretical density.

During presintering, but in particular during the complete sintering, the heating of the parts should be effected exclusively by convection, without any heating by radiative heat. This is to ensure that the completely sintered component parts exhibit a very high dimensional accuracy. Measurements have shown that the parts can be manufactured with a precision in the region between 1 µm and 2 µm, which ensures a high-precision degree of fit of the parts relative to each other.

During the production of the parts themselves one can employ a combination of milling and lathing work, which yields advantages in production technique and consequently cost savings.

The invention is also characterized by a constructional element produced using the above-described method, whereby the first component is a casing with an opening, through which passes as second component a plunger rod with a plunger, whereby the effective cross-section of the opening is smaller than the cross-section of the plunger positioned inside the casing.

The invention is further characterized by a constructional element produced using the above-described method, whereby a shaft—preferably flanged—constitutes the second component and a section of the shaft is surrounded by a pierced disk as the first component, whereby this section exhibits an offset relative to the shaft axis that is—or the shaft possesses sections with effective dimensions that are—greater than the opening of the unsintered-state disk, through which the shaft passes.

The invention is further characterized by a constructional element that is a dental implant with an implant component that carries a dental structure and constitutes the second component, with an opening, through which passes a bolt as the first component, whereby the bolt possesses widened ends with respective cross-sections that are greater than the effective cross-section of the opening.

Further details, advantages, and features of the invention can not only be found in the claims and the characteristic features contained therein, on their own and/or in combination, but also in the following description of a preferred embodiment example illustrated in the figures.

FIG. 4 shows a joint socket with joint in the unsintered state.

FIG. 5 shows the joint socket of FIG. 4 in the unsintered state and the joint in the sintered state.

FIG. 6 shows the joint socket and the joint of FIGS. 4 and 5 in the sintered state.

Figure 1:
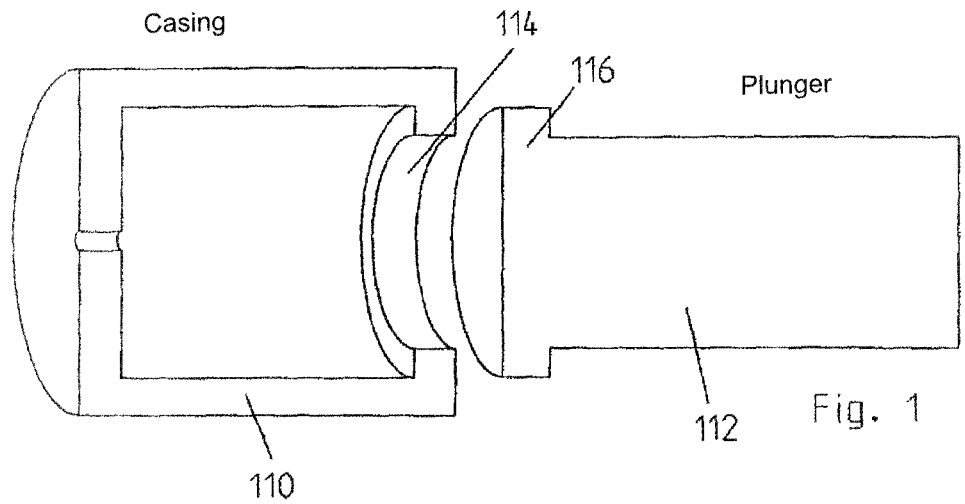
FIG. 1 illustrates the casing and plunger of a pump in an unsintered state.

The principles of the method according to the invention for producing multipart assemblies is to be explained with the help of the illustrations in the drawing, whereby high precision of fit and desired sealing are provided between the interlocking parts of the assemblies.

Figure 2:
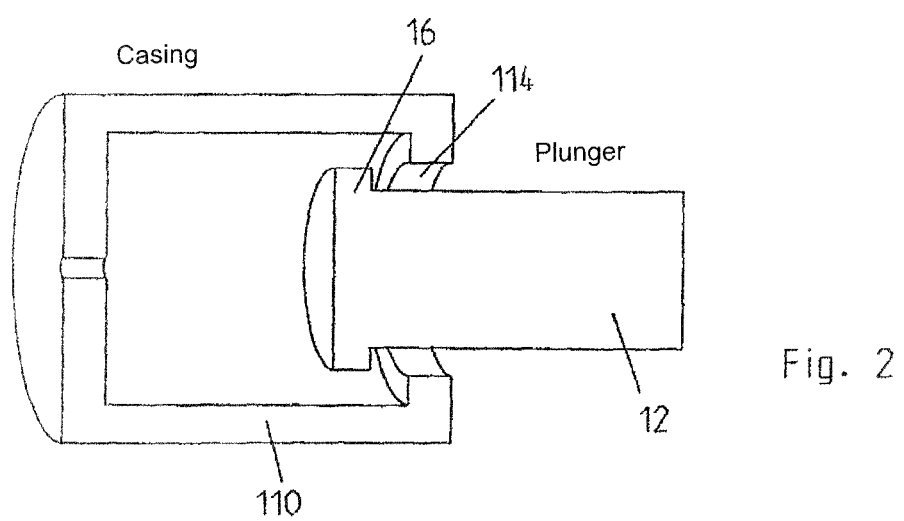
FIG. 2 shows the casing in the unsintered state and the plunger in the sintered state.
Figure 3:
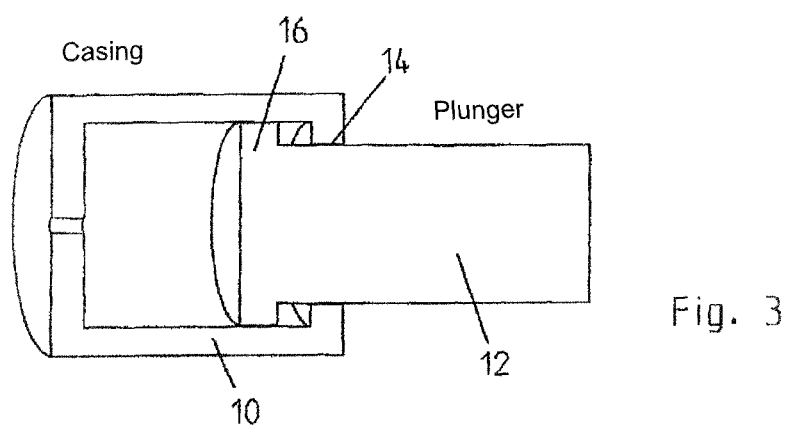
FIG. 3 shows the casing with the plunger moveable in the former, in the completely sintered state.

The method according to the invention is explained with the help of FIGS. 1 to 3, which illustrate a schematic drawing of a pump, which consists of a casing 10 and a plunger 12.

FIG. 3 illustrates the final fit of the plunger 12 and the casing 10, whereby the plunger 12 passes through an opening 14 of the casing 10 and its head 16 is movable back and forth within the casing 10. The head 16 possesses an outside diameter that is greater than that of the opening.

To obtain an equivalent assembly using state of technology methods, the casing has to consist of two parts in order to be able to position the plunger with its head in the interior of the casing. However, in accordance with the invention it is possible for the casing 10 to be embodied as a single part, since one utilizes the characteristics of ceramic materials that significantly shrink during sintering.

Both the plunger 12 and the casing 16 consist of oxide ceramic material, in particular of zirconia, which is available from the firm TOSOH under the trade name TZ-3YB or TZ-3YB-E. The corresponding zirconia powder material is pressed, in particular using isostatic pressing at a pressure of 200 MPa. The blanks produced in this manner are subsequently machined. This can be accomplished by lathing, milling, or a combination thereof. This produces parts with geometries that relative to that of the completely sintered plunger 12 or casing 10 are enlarged by a scaling factor that compensates for the shrinkage during sintering. The components (shaped parts) of the blank that correspond to the final component parts 10, 12 or sections 14, 16 thereof are labelled by reference labels 110, 112, 114, 116 in FIG. 1.

FIG. 1 illustrates that the components 110, 112 can not engage into each other, since the plunger head 116 is larger than the inside diameter of opening 114.

If the components 110, 112 are milled or lathed from a blank, it also becomes possible to use as blank a presintered body that is then machined.

Irrespectively, the plunger 112 with plunger head 116 composed of the blank or the presintered blank is completely sintered in a subsequent processing step. This preferably is performed at a temperature in the vicinity of 1500° C. for a duration of 2 hours. Prior to that one carries out a presintering, which is performed at a temperature of approximately 800° C. for a duration of 2 hours as well.

During the heat treatment, i.e. the complete sintering or presintering, care should be taken that the blanks are heated exclusively by convection and not by direct admission of thermal radiation.

As a result of the shrinkage, the dimensions of the plunger 112 change in such a way that the head 16 can pass through the opening 114 of the casing 110, as is illustrated in FIG. 2. This is followed by another complete sintering step according to the above-described processing mode, as a result of which the casing 110 shrinks to achieve the desired geometry match to the plunger 12 and the plunger head 16. The size of the plunger 112 is not changed.

In accordance with the invention, the components of the multipart assemblies are sintered partially independent of each other, in order to be assembled in different sinter states, which facilitates fitting the parts into place.

Since the individual components can be produced with high precision, the final geometry of the multipart assembly is consequently just as precise, so that a defined geometrical correspondence is ensured.

The method according to the invention shall also be explained in more detail with the help of the examples illustrated in FIGS. 4 to 8, whereby the fabrication of the individual elements can be performed in accordance with the above description.

FIGS. 4 to 6 illustrate how a joint 26 with joint ball 20 is introduced with a precise fit into a seat 24 of a joint socket 22, whereby both the joint 26 and the joint socket 22 consist of oxide ceramic material. These elements are shown as blanks in FIG. 4, where they are labelled by reference labels 120, 122, 124, 126. In this state, the joint ball 126 does not fit into the seat 124 of the joint socket 122. Rather, the elements 120, 122 exhibit a geometry that relative to the completely sintered joint 20 and joint socket 22 is enlarged by a scaling factor that compensates for shrinkage during sintering. Subsequently the joint 120 is sintered so that its ball 20 can be introduced into the opening 124 of the joint socket 122. Subsequently, the joint socket 122 is sintered together with the completely sintered joint ball 20 that was inserted into the opening 124, to achieve the desired precisely fitting connection of joint 20 and joint socket in accordance with FIG. 6.

Figure 7:
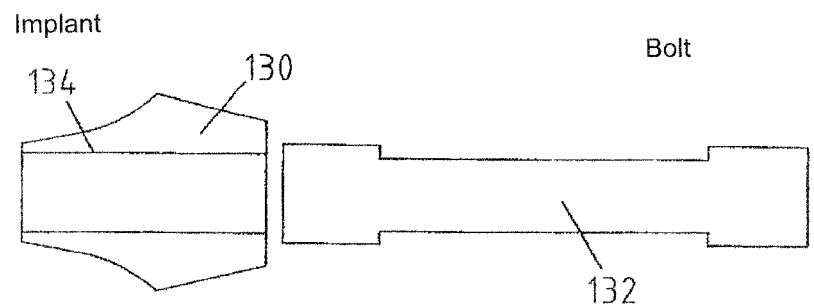
FIG. 7 illustrates an implant and a bolt in the unsintered state.
Figure 8:
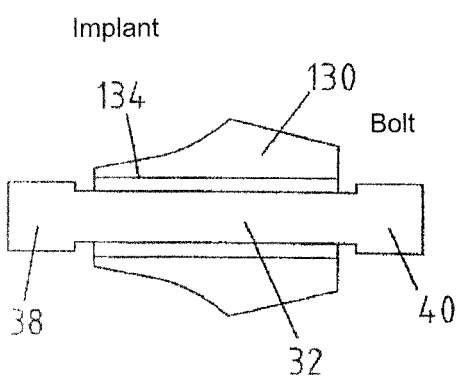
FIG. 8 shows the implant of FIG. 7 in its unsintered state and the bolt in a sintered state.
Figure 9:
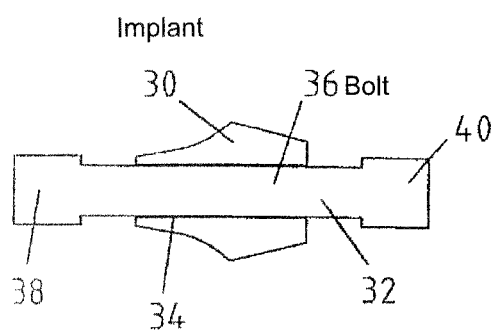
FIG. 9 shows the implant and the bolt of FIGS. 7 and 8 in the sintered state.

According to the invention's teaching, a high accuracy of fit can also be achieved between an implant 30 and a bolt 32, which passes with its barrel 36 through an opening 34 and at its ends possesses heads 38, 40, with diameters that are greater than the diameter of the opening 34. To facilitate an appropriate joining of implant 30 and bolt 32, one at first in accordance with the teachings of the invention produces blanks of the implant 130 and the bolt 132, which are schematically illustrated in FIG. 7. Now the bolt 132 is sintered. The dimensions of opening 134 and heads 138, 140 are matched to each other in such a manner that after the shrinkage occurring during sintering, the heads 38, 40 possess a diameter that is smaller than the opening 134 in the implant 130 as a blank, as illustrated in FIG. 8. After the completely sintered bolt 32 has been inserted into the opening 134 of the not completely sintered implant 130, i.e. the heads 38, 40 project laterally beyond the implant 130, a complete sintering is performed, which—as shown in FIG. 9—results in the bolt 32 passing through the implant 30 with a precise fit and with a possibly desired clearance.

Figure 10:
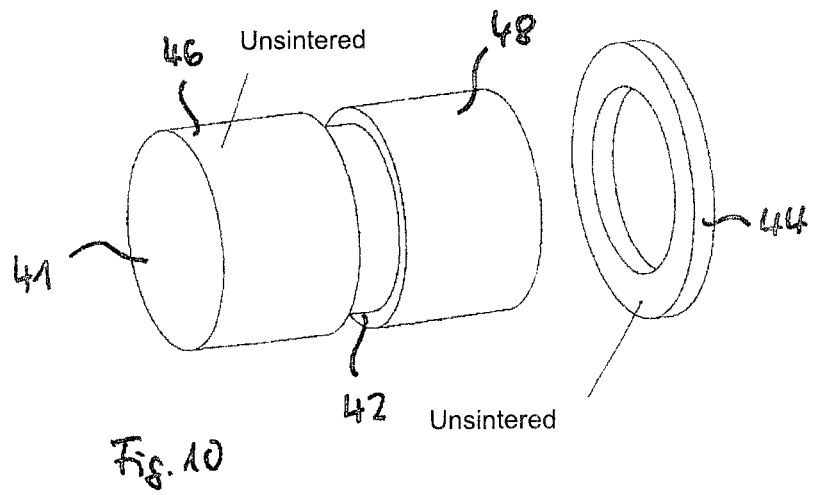
FIG. 10 shows a shaft with a ring in unsintered condition.
Figure 11:
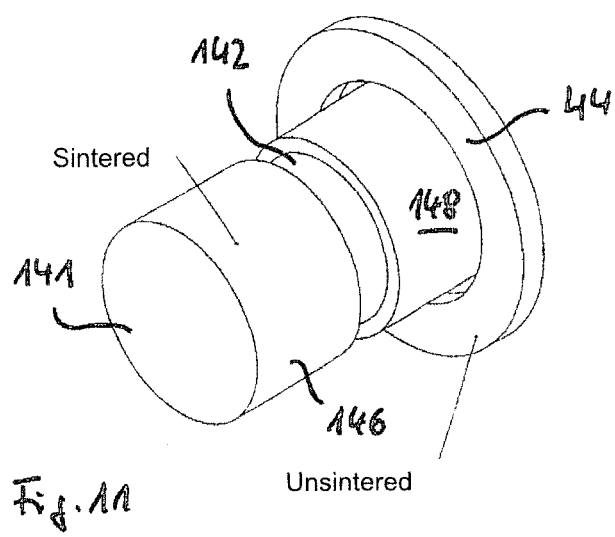
FIG. 11 illustrates the shaft of FIG. 10 in a sintered state.
Figure 12:
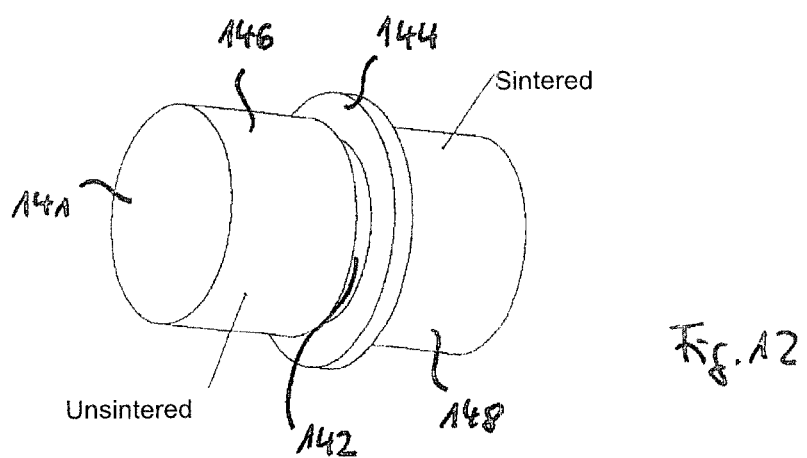
FIG. 12 illustrates the shaft and the ring of FIGS. 10 and 11 in a sintered state.

FIGS. 10 to 12 show a purely schematic representation of a further assembly, with elements consisting of completely sintered oxide ceramic material, whereby the joining together is accomplished as follows: a first part is completely sintered while the second part is not sintered or presintered, whereupon both parts are completely sintered together. FIG. 10 illustrates a section of a shaft 41, which has a groove 42. In so far, it could also be referred to as a flanged shaft. In order to place into the groove 42 a single-part ring 44, which possesses an inside diameter in its sintered state that is smaller than the shaft 41 sections 46, 48 bordering the groove 42 in the completely sintered state, the invention teaches to proceed as follows: at first the unsintered or presintered shaft 41 is sintered completely (shaft 141 in FIG. 11). As a result of the sintering, the shaft 41 experiences shrinkage. The ring 44 in its unsintered or presintered state possesses an inside diameter that is greater than the respective diameters of the sections 146 and 148 that border the groove 142 of the completely sintered shaft 141. Now the ring 44 is aligned with the groove 142, to subsequently completely sinter the ring 44 together with the sintered shaft 141. During this, the already sintered shaft 141 does not experience any further shrinkage. Only the ring 144 experiences shrinkage. The inside diameter of the ring 44 is chosen in such a way that—on account of the shrinkage occurring during complete sintering—the final dimensions will be such that the inside diameter of the sintered ring 144 is smaller than the outside diameters of the adjoining sections 146, 148. This results in a joining of the component parts 141, 144, which now are connected in a non-detachable manner, without the need to embody the ring 144 as a multipart component for assembly.

The invention claimed is:

1. A method for manufacturing a multipart assembly of sintered oxide ceramic material, comprising one first component, which at least partially surrounds one second component, such that detaching the first component from the second component is impossible without destroying the first and/or second component, comprising the steps of:
    producing a single-part first shaped part and a single-part second shaped part from an oxide ceramic blank, whereby the first shaped part and the second shaped part are enlarged, relative to the first component and the second component, by a scaling factor that compensates for shrinkage during sintering,
    completely sintering the second shaped part to produce the second component, and
    assembling the second component with the first shaped part and subsequently sintering them together,
    wherein as the first shaped part one employs a shaped part with an opening, whose effective cross section after sintering is smaller than the effective cross section of the second component in front of and behind the opening, in an area not contained within the opening;
    the sintered first shaped part and the sintered second shaped part being movable with respect to each other.

2. The method of claim 1, wherein the ceramic blank is a green blank of pressed oxide ceramic powder.

3. The method of claim 2, wherein the green blank is presintered at a temperature $T_1$ with $T_1 \geqq 450°$ C. for a duration $t_1$ with $0.5 \text{ h} \leqq t1 \leqq 6 \text{ h}$.

4. The method of claim 1, wherein oxide ceramic powder is pressed by axial or isostatic pressing at a pressure p with $150 \text{ MPa} \leqq p \leqq 350 \text{ MPa}$.

5. The method of claim 1, wherein the ceramic blank is a presintered blank of pressed oxide ceramic powder material.

6. The method of claim 5, wherein the presintered blank is dense-sintered at a temperature $T_2$ with $1300°\,C. \leqq T_2 \leqq 1650°\,C.$ for a duration $t_2$ with $1\,h \leqq t_2 \leqq 3\,h$.

7. The method of claim 1, wherein the oxide ceramic powder is at least one metal oxide powder selected from the group consisting of partially stabilized zirconia, $Al_2O_3$, $TiO_2$, $MgO$, $Y_2O_3$, $BaTiO_3$, zirconia, zirconia mixed crystal powder.

8. The method of claim 1, wherein the zirconia mixed crystal powder consists of:
   90-98% by weight zirconia
   0-4% by weight hafnium oxide
   1-7% by weight yttrium oxide
   0-1% by weight one of the oxides of the elements aluminum, gallium, germanium, zinc, lead, the lanthanides
   0-2% by weight oxidation-dyeing additives.

9. The method of claim 8, wherein the oxidation-dyeing additives are selected from the group consisting of $Er_2O_3$, $Pr_6O_{11}$ and $Fe_2O_3$.

10. The method of claim 1, wherein the blank is dense-sintered to 90% to 100% of the theoretical density.

11. The method of claim 1, wherein the green blank is presintered at a temperature $T_1$ where $600°\,C. \leqq T1 \leqq 1200°\,C.$ 12. The method of claim 1, wherein the blank is dense-sintered to 96% to 100% of the theoretical density.

13. The method of claim 1, wherein sintering or presintering is carried out by convection and not by direct thermal radiation.

14. The method of claim 1, wherein the blank or presintered blank comprises a plunger with plunger rod.

15. The method of claim 14, wherein the sintering is carried out at a temperature of about 1500° C. for 2 hours.

16. The method of claim 14, wherein the plunger with plunger rod is presintered at a temperature of about 800° C. for 2 hours.

17. A method for manufacturing a multipart assembly of sintered oxide ceramic material, comprising one first component, which at least partially surrounds one second component, such that detaching the first component from the second component is impossible without destroying the first and/or second component, comprising the steps of:
   producing a single-part first shaped part and a single-part second shaped part from an oxide ceramic blank, whereby the first shaped part and the second shaped part are enlarged, relative to the first component and the second component, by a scaling factor that compensates for shrinkage during sintering,
   completely sintering the second shaped part to produce the second component, and
   assembling the second component with the first shaped part by inserting the second component into the first shaped part in a longitudinal direction, and subsequently sintering them together,
   wherein as the first shaped part one employs a shaped part with an opening, whose effective cross section after sintering is smaller than the effective cross section of the second shaped part after sintering in a region that extends within the first component;
   the sintered first shaped part and the sintered second shaped part being movable in the longitudinal direction with respect to each other.

18. The method of claim 17, wherein the ceramic blank is a green blank of pressed oxide ceramic powder.

19. The method of claim 17, wherein oxide ceramic powder is pressed by axial or isostatic pressing at a pressure p with $150\,MPa \leqq p \leqq 350\,MPa$.

20. The method of claim 17, wherein the ceramic blank is a presintered blank of pressed oxide ceramic powder material.

21. The method of claim 18, wherein the green blank is presintered at a temperature $T_1$ with $T_1 \geqq 450°\,C.$ for a duration $t_1$ with $0.5h \leqq t1 \leqq 6\,h$.

22. The method of claim 20, wherein the presintered blank is dense-sintered at a temperature $T_2$ with $1300°\,C. \leqq T_2 \leqq 1650°\,C.$ for a duration $t_2$ with $1h \leqq t_2 \leqq 3h$.

23. The method of claim 17, wherein the oxide ceramic powder is at least one metal oxide powder selected from the group consisting of partially stabilized zirconia, $Al_2O_3$, $TiO_2$, $MgO$, $Y_2O_3$, $BaTiO_3$, zirconia, zirconia mixed crystal powder.

24. The method of claim 17, wherein the zirconia mixed crystal powder consists of:
   90-98% by weight zirconia
   0-4% by weight hafnium oxide
   1-7% by weight yttrium oxide
   0-1% by weight one of the oxides of the elements aluminum, gallium, germanium, zinc, lead, the lanthanides
   0-2% by weight oxidation-dyeing additives.

25. The method of claim 17, wherein the blank is dense-sintered to 90% to 100% of the theoretical density.

26. The method of claim 17, wherein the green blank is presintered at a temperature $T_1$ where $600°\,C. \leqq T1 \leqq 1200°\,C.$ 27. The method of claim 24, wherein the oxidation-dyeing additives are selected from the group consisting of $Er_2O_3$, $Pr_6O_{11}$ and $Fe_2O_3$.

28. The method of claim 17, wherein the blank is dense-sintered to 96% to 100% of the theoretical density.

29. The method of claim 17, wherein sintering or presintering is carried out by convection and not by direct thermal radiation.

30. The method of claim 17, wherein the blank or presintered blank comprises a plunger with plunger rod.

31. The method of claim 30, wherein the sintering is carried out at a temperature of about 1500° C. for 2 hours.

32. The method of claim 30, wherein the plunger with plunger rod is presintered at a temperature of about 800° C. for 2 hours.

* * * * *